US006413431B1

(12) United States Patent
Abedi (10) Patent No.: US 6,413,431 B1
(45) Date of Patent: Jul. 2, 2002

(54) HPLC METHOD FOR PURIFYING ORGANIC COMPOUNDS

(75) Inventor: Jaleh Abedi, Raleigh, NC (US)

(73) Assignee: Scynexis Chemistry & Automation, Inc., Durham, NC (US)

( * ) Notice: Subject to any disclaimer, the term of this patent is extended or adjusted under 35 U.S.C. 154(b) by 50 days.

(21) Appl. No.: 09/625,606

(22) Filed: Jul. 26, 2000

Related U.S. Application Data (60) Provisional application No. 60/148,153, filed on Aug. 10, 1999.

(51) Int. Cl.[7] .............................................. B01D 15/08
(52) U.S. Cl. ...................... 210/656; 210/659; 210/143; 210/198.2; 436/161; 436/518
(58) Field of Search ................................ 210/635, 656, 210/659, 143, 198.2; 436/161, 518

(56) References Cited

U.S. PATENT DOCUMENTS

| | | | | |
|---|---|---|---|---|
| 3,589,867 A | | 6/1971 | Heinz et al. ............... 23/230 R |
| 3,680,967 A | | 8/1972 | Engelhardt .................. 356/246 |
| 3,853,010 A | | 12/1974 | Christen et al. .............. 73/423 |
| 4,579,663 A | * | 4/1986 | Poile .......................... 210/656 |
| 4,719,017 A | * | 1/1988 | Uchino ....................... 210/656 |
| 4,798,095 A | | 1/1989 | Itoh ......................... 73/863.01 |
| 4,835,707 A | | 5/1989 | Amano et al. .............. 364/497 |
| 5,203,992 A | * | 4/1993 | Drouen ..................... 210/198.2 |
| 5,209,853 A | * | 5/1993 | Lynch ........................ 210/656 |
| 5,267,178 A | | 11/1993 | Berner ....................... 364/498 |
| 5,273,715 A | | 12/1993 | Bridgham et al. ............ 422/63 |
| 5,301,261 A | | 4/1994 | Poole et al. .................. 395/82 |
| 5,324,483 A | | 6/1994 | Cody et al. ................. 422/131 |
| 5,409,611 A | * | 4/1995 | Kauver ....................... 210/635 |
| 5,434,971 A | | 7/1995 | Lysakowski, Jr. ........... 395/200 |
| 5,463,564 A | | 10/1995 | Agrafiotis et al. .......... 364/496 |
| 5,489,678 A | | 2/1996 | Fodor et al. ................ 536/22.1 |
| 5,491,096 A | * | 2/1996 | Sportsman ................. 436/518 |
| 5,506,805 A | | 4/1996 | Sugarman et al. .......... 422/131 |
| 5,525,464 A | | 6/1996 | Drmanac et al. .............. 435/6 |
| 5,527,681 A | | 6/1996 | Holmes .......................... 435/6 |
| 5,541,061 A | | 7/1996 | Fodor et al. ................... 435/6 |
| 5,545,531 A | | 8/1996 | Rava et al. .................... 435/6 |
| 5,547,839 A | | 8/1996 | Dower et al. .................. 435/6 |
| 5,552,270 A | | 9/1996 | Khrapko et al. .............. 435/6 |
| 5,556,762 A | | 9/1996 | Pinilla et al. ............... 435/7.21 |
| 5,574,656 A | | 11/1996 | Agrafiotis et al. .......... 364/500 |
| 5,595,664 A | | 1/1997 | Sanford et al. ............. 210/656 |
| 5,609,826 A | | 3/1997 | Cargill et al. ................ 422/99 |
| 5,639,603 A | | 6/1997 | Dower et al. .................. 435/6 |
| 5,641,634 A | | 6/1997 | Mandecki ...................... 435/6 |
| 5,658,799 A | | 8/1997 | Choperena et al. .......... 436/50 |
| 5,670,054 A | * | 9/1997 | Kibber ....................... 210/656 |
| 5,679,582 A | * | 10/1997 | Bowie ........................ 436/518 |
| 5,679,773 A | | 10/1997 | Holmes ....................... 530/334 |
| 5,684,711 A | | 11/1997 | Agrafiotis et al. .......... 364/500 |
| 5,690,893 A | | 11/1997 | Ozawa et al. ................ 422/67 |
| 5,693,292 A | | 12/1997 | Choperena et al. .......... 422/67 |
| 5,708,153 A | | 1/1998 | Dower et al. ............... 536/221 |
| 5,712,171 A | | 1/1998 | Zambias et al. ............ 436/518 |
| 5,736,412 A | | 4/1998 | Zambias et al. ............ 436/518 |
| 5,741,462 A | | 4/1998 | Nova et al. ................. 422/681 |
| 5,757,659 A | | 5/1998 | Arai et al. .................. 364/497 |
| 5,766,481 A | * | 6/1998 | Zambias ..................... 210/656 |
| 5,772,962 A | | 6/1998 | Uchida et al. ................ 422/67 |
| 5,798,035 A | | 8/1998 | Kirk et al. ................... 205/335 |
| 5,807,754 A | | 9/1998 | Zambias et al. ............ 436/518 |
| 5,827,946 A | * | 10/1998 | Klee ........................ 210/198.2 |
| 5,862,514 A | | 1/1999 | Huse et al. ................... 702/22 |
| 5,874,214 A | | 2/1999 | Nova et al. .................... 435/6 |
| 5,901,069 A | | 5/1999 | Agrafiotis et al. ...... 364/528.03 |
| 5,925,562 A | | 7/1999 | Nova et al. ............... 435/287.1 |
| 5,938,932 A | | 8/1999 | Connelly et al. ........... 210/659 |
| 5,939,612 A | * | 8/1999 | Wylie ......................... 210/656 |
| 5,942,387 A | | 8/1999 | Hollinshead .................. 435/5 |
| 5,948,360 A | | 9/1999 | Rao et al. ..................... 422/65 |
| 5,993,662 A | | 11/1999 | Garr et al. .................. 210/656 |
| 6,054,047 A | * | 4/2000 | Hindsgaul ................ 210/198.2 |

FOREIGN PATENT DOCUMENTS

| | | | |
|---|---|---|---|
| DE | 196 05 814 | 8/1997 | ................. 210/659 |
| EP | 08 82500 | 12/1998 | ................. 210/659 |
| EP | 0 903 176 | 3/1999 | ................. 210/659 |
| FR | 2 760 843 | 9/1998 | ................. 210/659 |
| WO | 95 1559 | 1/1995 | ................. 210/659 |
| WO | 96 05488 | 2/1996 | ................. 210/659 |

OTHER PUBLICATIONS

Bishop, C.A., et al., "The Preparative Separation of Synthetic Peptides on Reversed–Phase Silica Packed in Radially Compressed Flexible–Walled Columns," *J. Liquid Chromatography*, 4(4): 661–680, 1981.

Bishop, C.A., et al., "High Performance Liquid Chromatography of Amino Acids, Peptides and Proteins XXI. The application of preparative reversed–phase high–performance liquid chromatography for the purification of a synthetic underivatised peptide," *Journal of Chromatography*, 192: 222–227, 1980.

Brenner, S., et al., "Encoded combinatorial chemistry", *Proc, Nat'l. Acad, Sci. USA*, 89: 5381–5383, 1992.

DeWitt, S. H., et al., "Combinatorial Organic Synthesis Using Parke–Davis's Diversomer Method", *Acc. Chem. Res.*, 29(3): 114–122, 1996.

Griffey, R. H., et al., "Rapid Deconvolution of combinatorial Libraries using HPLC Fractionation", *Tetrahedron, NL, Elsevier Sci. Pub.*, 54(16): 4067–4076, 1998.

Harris, S., et al., "High Throughput Analysis & Purification: The new Paradigm", *MDS Panlabs*, 1–13, 1998.

(List continued on next page.)

*Primary Examiner*—Ernest G. Therkorn
(74) *Attorney, Agent, or Firm*—Burns Doane Swecker & Mathis LLP (57) ABSTRACT

An HPLC method which purifies and/or characterizes large numbers of related compounds, for example, those prepared for use in combinatorial libraries, is disclosed. The compounds are purified on a semi-preparative or preparative scale, enabling rapid preparation of combinatorial libraries with minimal operator involvement, and, preferably, with a purity greater than about 90%.

13 Claims, 2 Drawing Sheets

OTHER PUBLICATIONS

Josses, P, et al., "Carrying out Multiple Reactions in Organic Synthesis with a Robot", *Advances in Laboratory Automation Robotics*, 5: 463–475, 1990.

Kaliszan, R., et al., "Quantitative Structure–Chromatographic Retention Relationships", *Chemical Analysis*, 91: 234–278 (Chapter 11), Wiley and Sons, New York, 1987.

Kibbey, C. E., "An Automated System for the Purification of Combinatorial libraries by Preparative LC/MS", *Laboratory Robotics and Automation*, 9: 309–321, 1997.

Knighton, D. R., et al., "Facile, Semi–Preparative, High–Performance Liquid Chromatographic Separation of Synthetic Peptides Using Ammonium Bicarbonate Buffers," *Journal of Chromatography*, 249: 193–198, 1982.

Lindsey, J. S., "A retrospective on the automation of laboratory synthetic chemistry", *Laboratory Automation & Information Management*, 17(1): 15–45, 1992.

Mirrlees, M.S., et al., "Direct Measurement of Octanol–Water Partition Coefficients by High–Pressure Liquid Chromatography," *J. Med. Chem.*, 19(5): 615–619, 1976.

Rotstein, S., et al., "GroupBuild: A Fragment–Based Method for *De Novo* Drug Design", *J. Med. Chem.*, 36: 1700–1710, 1993.

Rudge, D. A., "The automation of solution phase synthetic chemistry using XP Zymate™ laboratory robotic systems", *Laboratory Automation & Information Management*, 33(2): 81–86, 1997.

Schultz, L., et al., "High Throughput Purification of Combinatorial Libraries", *Bio & Med. Chem. Ltrs.*, 8: 2409–2414, 1998.

Testa, B., "The Concept of Molecular Structure in Structure in Structure–Activity Relationship Studies and Drug Design", *Med. Res. Rev.*, 11 (1): 38–48, 1991.

"Techniques and Experiments for Organic Chemistry", *2nd Edition*, 56–60, 1977.

Weller, H. N., et al., "High throughput analysis and purification in support of automated parallel synthesis", *Molecular Diversisty*, 3: 61–70, 1997.

Zeng, L., et al., "Automated analytical/preoperative high–performance liquid chromatography–mass spectrometry system for the rapid characterization and purification of compound libraries", *J. of Chrom. A*, (Elseiver science B.V.) 794: 3–13, 1998.

* cited by examiner

HPLC METHOD FOR PURIFYING ORGANIC COMPOUNDS

This application claims priority under 35 U.S.C. §§119 and/or 365 to U.S. application Ser. No.: 60/148,153 filed in United States Patent and Trademark Office on Aug. 10, 1999; the entire content of which is hereby incorporated by reference.

Field of the Invention

The present invention generally relates to the purification and/or characterization of libraries of compounds, for example, combinatorial and lead generation libraries.

BACKGROUND OF THE INVENTION

Currently, there are many general methods for purifying synthetic compounds. These methods generally involve purifying a single target compound from multiple impurities.

Compounds are currently being prepared in relatively large numbers in combinatorial and lead generation libraries. Often, compounds are synthesized in multi-well plates or multi-tube arrays, with the number of related compounds numbering in the thousands. It is difficult to purify and characterize the libraries of compounds at the rate at which they are synthesized.

One method for purifying large numbers of compounds involves a repetitive method of chromatographing individual compounds. This constitutes a full cycle of synthesis, work-up, and purification for each molecule. Often, a large amount of time is spent developing an appropriate purification method for the compounds to be purified.

It would be advantageous to develop efficient methods for purifying and/or characterizing libraries of compounds which are applicable to a wide variety of organic compounds. The present invention provides such methods.

SUMMARY OF THE INVENTION

Methods for purifying and/or characterizing compounds, particularly libraries of compounds such as combinatorial or lead generation libraries, are disclosed. Purification devices capable of being used in the method are also disclosed.

The method is premised on the discovery that structurally similar compounds, such as those in combinatorial and lead generation libraries, often have roughly similar retention factors (Rfs) on thin layer chromatography (TLC) plates and retention times on high performance liquid chromatography (HPLC) columns. The method uses this discovery to determine optimum conditions for purifying a library of similar compounds.

For a given column packing, solvent system, and flow rate, most compounds tend to elute to a certain degree from an analytical and/or preparative HPLC column. Similarly, most compounds move to a certain degree on TLC plates. While some compounds do not move at all (Rf=0), others move with a low Rf (for example, 0.05<Rf<0.2), a medium Rf (for example, 0.2<Rf<0.8), or a high Rf (for example, Rf>0.8). One can readily determine a series of three or more, preferably four or more, zones of Rfs, or, in the case of analytical HPLCs, a series of zones of retention times, in which the majority of compounds in the library will elute (in the case of an analytical HPLC) or move (in the case of a TLC), for example, low, medium and high Rfs on a TLC plate. These zones can be correlated to preparative or semi-preparative methods for performing preparative or semi-preparative HPLCs.

For a given analytical HPLC and/or TLC protocol, a set of preparative HPLC conditions can be identified wherein compounds in one zone can be separated from compounds in other zones. Accordingly, if all or substantially all of the compounds in a representative sample of a library of compounds is present in the same zone, the library can be purified using the same HPLC protocol, which can be readily correlated to a zone on the TLC and/or analytical HPLC.

The methods described herein involve evaluating a representative sample of compounds from a library of compounds, such as a combinatorial or lead generation library, by TLC and/or analytical HPLC, to determine which zone they move on the TLC plate and/or elute off the analytical HPLC column. Once the zone is identified, a correlated preparative or semi-preparative method is used to purify the library.

Appropriate conditions for purifying a library of compounds can be worked out by route scouting a representative sample of the library for a given analytical HPLC column, solvent system and flow rate, and/or a given TLC backing and solvent system. A correlated preparative or semi-preparative HPLC method can be applied to purify the library of compounds without having to change the purification parameters, so that a single method can be applied to the entire library.

A suitable sample size is typically on the order of between 2 and 5% of the library, depending on the diversity of the compounds in the library. This approach is referred to herein as "route scouting," since one is scouting for an appropriate purification route.

Preferably, both the TLC and the HPLC are performed on the representative sample of compounds. It is also preferred to perform preparative or semi-preparative HPLC on a sample of compounds from the library before purifying the entire library. This allows one to verify that the conditions are suitable for purifying the entire library, for example, by determining the purity of the compounds in the representative sample. Also, one can perform a TLC on between 10 and 100%, preferably between 50 and 100% of the library and compare the TLC to that in the representative sample. By performing a TLC on the entire library and/or determining the purity of a representative sample of compounds, one can ensure that the majority of the library can be adequately purified. If the purity is not adequate on the representative sample, or if the TLC of the library does not sufficiently match that of the representative sample, alternative preparative HPLC conditions can be used.

The representative sample should encompass, if possible, the most polar and least polar compounds synthesized in the library, to help ensure that the method is applicable for the entire library.

The method described herein results in substantial time savings in the purification and characterization of libraries of compounds, and can provide compounds with greater than 90% purity.

DETAILED DESCRIPTION

Compounds are often synthesized in the form of combinatorial libraries, which are often in the form of multi-well plates or multi-tube arrays. A major bottleneck in the synthesis, purification and evaluation of the compounds is determining appropriate purification conditions for the compounds. The methods described herein detail how entire libraries of structurally related compounds can be purified.

The methods are premised on the discovery that structurally similar compounds, such as those in combinatorial and lead generation libraries, often have roughly similar retention times on thin layer chromatography (TLC) plates and on high performance liquid chromatography (HPLC) columns. For a given sorbent, solvent system, and flow rate, most compounds tend to move a certain degree on a plate. For example, some compounds do not move much at all (Rf near 0). Others move with a low Rf (for example, between 0.05 and 0.2), a medium Rf (for example, between 0.2 and 0.8), or a high Rf (great than 0.8). The methods use this discovery to determine optimum conditions for purifying a library of similar compounds.

An advantage of the methods is that analytical HPLC is performed, if at all, only on a representative sample prior to performing preparative HPLC. Using the methods described herein, the purity of all or substantially all of the compounds purified via preparative HPLC can be greater than 90 percent.

DEFINITIONS

As used herein, the term "preparative HPLC" and like terms is meant an HPLC system which is capable of producing high (500 or more) microgram, milligram, or gram sized product fractions. The term "preparative" includes both preparative and semi-preparative columns, but is not intended to include analytical columns, which provide fractions in the nanogram to low microgram range.

As used herein, the term "mechanically actuatable" when referring to a switching valve is meant a valve whose different positions are selected by other than manual actuation, i.e., by computer selection. The actual mechanical actuation may be electric (i.e. a solenoid controlled valve), pneumatic (i.e. an air pressure controlled valve), hydraulic (a liquid pressure controlled valve), or any other equivalent means.

As used herein, an "HPLC compatible detector" is a detector suitable for use in an HPLC system which is capable of providing a detectable signal upon elution of a compound peak. For example, a detector capable of generating a signal when a compound elutes from the compound is an HPLC compatible detector. Where component absorbance varies widely, it may be necessary to utilize more than one detector. A detector capable of detecting a desired component is not an "incompatible" detector due to its inability to detect a non-desired peak.

A "waste reservoir" is a destination suitable for collecting eluate that does not include the compound of interest, for example, the solvent used to regenerate the column between runs or the eluate driven off the column before and after the compound of interest has eluted. Suitable waste reservoirs include flasks, bottles, or jugs.

HPLC Devices

Displacement chromatography (an example of which is HPLC) is based on the principle that in a sample the balance between stationary phase (SP) and mobile phase (MP) is shifted the direction of SP. Single components of a sample displace each other like a train and the displacing agent with the greater affinity to SP pushes this train by fractions out of the column. Gas chromatography, liquid chromatography and HPLC chromatography are some of the most well known examples of displacement chromatography.

An HPLC device typically includes at least the following components: a column, packed with a suitable stationary phase, a mobile phase, a pump for forcing the mobile phase through the column under pressure, and a detector for detecting the presence of compounds eluting off of the column. The devices can optionally include a means for providing for gradient elution, although such is not necessary using the methods described herein.

Routine methods and apparatus for carrying out HPLC separations are well known in the art, and are described, for example, in the following references: *J. Chromatography*, 192:222–227 (1980), *J. Liquid Chromatography* 4:661–680 (1981), and *J. Chromatography*, 249:193–198 (1982).

Suitable stationary phases are those in which the compound of interest elutes. Preferred columns are reverse phase columns, which may be natural (silica gel with alkyl chains of different lengths) or a synthetic crosslinked polymer (consisting of styrene and divinylbenzene). The particle size of the stationary phase is within the range from a few $\mu$m to several 100 $\mu$m. The most preferred stationary phase is a $C_{18}$ column.

Suitable detection devices include mass spectrometers and UV detectors. The methods described herein use both of these detectors to determine when sample should be detected.

The methods described herein often require the use of relatively high pressures (for example, up to approximately 2000 psi), depending on the pump head, column size, mobile phase and sorbent particle size. These pressures may be in excess of normal operating conditions for standard preparative HPLC. The methods also often require using flow rates of mobile phase (for example, in excess of 30 mL/min) in excess of those used in normal operating conditions for standard preparative HPLCs.

In some embodiments, methanol/water is used as the mobile phase. Methanol/water solvent systems are more viscous than otherwise equivalent systems employing acetonitrile/water (which are more commonly used, but which can be more costly). The increased viscosity tends to create a high back pressure, and can require the use of high pressure tubing as well as tubing with wider than normal internal diameters. Further, the use of column packings (sorbents) with relatively small particle sizes (for example, 5 microns or less) can cause back pressure, further mandating the use of wider tubings.

Purification Method

The method involves evaluating a representative sample of compounds from a library of structurally similar compounds by TLC and/or analytical HPLC to determine which zone they move on the TLC plate and/or elute off the analytical HPLC column. Once the zone is identified, a correlated preparative or semi-preparative method is used to purify the library.

One can determine a series of three or more zones of retention factors on a TLC plate and/or retention times on an analytical HPLC trace, and correlate a preparative HPLC protocol to each of the zones. The zones can be, for example, low, medium and high Rfs on a TLC plate, where low, medium and high are arbitrary terms which can be defined in any suitable manner such that they correspond to a correlated preparative or semi-preparative HPLC protocol which separates compounds in one zone from compounds in the other zones. For a given analytical HPLC and/or TLC protocol, a set of HPLC conditions can be identified wherein compounds in one zone can be separated from compounds in other zones.

Accordingly, if a TLC or analytical HPLC shows that all or substantially all (i.e., greater than 95%) of the compounds in a library of compounds are present in the same zone, they can all be purified using one correlated HPLC protocol.

As used herein, a representative sample is typically less than 10 percent of the library, more preferably, less than 5 percent of the library, and most preferably, between 2 and 5 percent of the library. The number of compounds in the sample depends on the diversity of the library (in terms of polarity, and, hence, the retention time on an HPLC column or retention factor on a TLC plate). The representative compounds should encompass, if possible, the most polar and least polar compounds synthesized in the library, to help ensure that the method is applicable for all compounds in the library.

As used herein, a zone refers to a range of retention times or retention factors. For example, some compounds do not move much at all (Rf near 0). Others move with a low Rf (for example, between 0.05 and 0.2), a medium Rf (for example, between 0.2 and 0.8), or a high Rf (great than 0.8). Using a TLC and using these ranges of retention factors, three zones can be identified, low, medium and high. The zones can be correlated to preparative or semi-preparative HPLC conditions which purify compounds which move on the TLC plate with an Rf in the particular zone. A series of compounds was subjected to TLC and preparative HPLC using these representative zones, and the results are described in Example 1. A preferred solvent system for eluting compounds on a TLC plate is eighty percent methanol/20 percent water (v/v), and this is the solvent system which was used in Example 1.

Preferably, the purification protocol uses four or more zones. One of skill in the art can readily and subjectively determine an appropriate set of zones, taking into consideration a range of retention factors on a TLC plate using a given solvent system, or a given range of retention times on an analytical HPLC column using a given column packing and solvent system, and correlate these zones to effective preparative HPLC conditions to purify all compounds which fall into a particular zone.

Using the methods described herein, one can quickly identify a set of conditions which applies broadly to the library. This results in a significantly quicker turnaround time for purifying the library when compared with traditional methods which involve performing an analytical HPLC on the entire library before subjecting the library to preparative HPLC conditions.

Appropriate conditions for purifying a library of compounds can be worked out by route scouting a representative sample of the library for a given analytical HPLC column, solvent system and flow rate, and/or a given TLC backing and solvent system. A correlated preparative or semi-preparative HPLC method can be applied to purify the library of compounds without having to change the purification parameters, so that a single method can be applied to the entire library.

Preferably, both the TLC and the HPLC are performed on the sample of compounds. It is also preferred to perform preparative or semi-preparative HPLC on a sample of compounds from the library before purifying the entire library. This allows one to verify that the conditions are suitable for purifying the entire library, for example, by determining the purity of the compounds in the representative sample. Also, one can perform a TLC on between 10 and 100%, preferably between 50 and 100% of the library and compare the TLC to that in the representative sample. By performing a TLC on the entire library and/or determining the purity of a representative sample of compounds, one can ensure that the majority of the library can be adequately purified. If the purity is not adequate on the representative sample, or if the TLC of the library does not sufficiently match that of the representative sample, alternative preparative HPLC conditions can be used.

The method described herein results in substantial time savings in the purification and characterization of libraries of compounds, and can provide compounds with greater than 90% purity.

In one embodiment, the method involves performing the following steps:

a) selecting a library of compounds to be purified b) performing a TLC and/or an analytical HPLC on a representative sample of the library, which sample comprises less than ten percent of the library,     c) determining a correlated preparative HPLC method depending on how the representative sample elutes off the analytical HPLC column (identifying a zone of retention times) and/or the sample moves on a TLC plate (identifying a zone of retention factors), and     d) purifying all or substantially all of the library,     wherein the correlated preparative HPLC method is determined based on a correlation between three or more zones of retention times if analytical HPLC is performed and/or three or more zones of retention factors if TLC is performed, such that if substantially all of the compounds in the representative sample fall within a particular zone, a correlated preparative HPLC protocol can be used to purify compounds that fall within the zone.

Preferably, both analytical HPLC and TLC are performed in step a. The representative sample is preferably purified via preparative HPLC before all or substantially all of the library is purified. After the representative sample is purified, the purity of the compounds in the sample is preferably determined. This provides a fast and effective means for checking the method to ensure that it works effectively.

After the purity is determined, one can optionally perform a TLC on between 10 and 100 percent of the library, preferably between 50 and 100 percent of the library, under the same or substantially the same conditions as the TLC performed in step a. This verifies that the purification conditions which apply to the representative sample apply also to the entire library.

By checking the purity of the representative sample and by performing a TLC on a larger portion of the library, one can verify that the technique adequately purified the compounds, and that the conditions apply broadly to the entire library. If the desired purity is not obtained, and/or if the TLC of the representative sample and the 10 to 100 percent of the library show that the compounds do move into the same zone, then alternative preparative HPLC protocols need to be determined. In some cases, a separate protocol may be applied to a portion of the library.

During the preparative HPLC of all or substantially all of the library, it is preferred that fraction collection is triggered by determining the presence of the compound of interest in a sample which is eluting off of the preparative HPLC column using UV and/or MS detection.

In one embodiment, libraries of compounds are purified by a) determining the Rf or retention time of a compound or a representative sample of compounds from a library of compounds by TLC or analytical HPLC, b) correlating the Rf or retention time to a set of preparative HPLC conditions with a set of parameters which correlates to the conditions used for the TLC or analytical HPLC, and c) performing preparative or semi-preparative HPLC on the compound or the compounds in the library, wherein
   i) a portion of the eluent from the preparative or semi-preparative HPLC column is sent to a UV detector and another portion of the eluent is sent to a mass spectrometer (MS);
   ii) the eluent is discarded until UV and/or MS indicates that the compound of interest is eluting,
   iii) the sample containing the compound of interest is characterized by MS,
   iv) the sample containing the compound of interest is collected;
   v) the column is washed with an appropriate solvent such that any impurities are removed from the column;
   vi) the column is re-equilibrated, and
   vii) the steps are repeated as necessary for each compound to be purified and/or characterized.

The methods allow collection of UV absorbance and MS data in the same time frame. Fraction collection by MS has several risks associated with it, including loss of desired compound due to miscalculation of molecular masses, formation of adducts, and loss of compounds that do not ionize under the conditions that are used. On the other hand, the advantage of fraction collection by MS is that only a few fractions are collected. The benefits of fraction collection by MS are obtained and the detriments are avoided by triggering fraction collection by both UV and MS. However, the difficulties associated with doing so are that it is difficult to trigger fraction by UV and use a high flow gradient. To ensure reliable splits of flow to the MS and the fraction collection, the back pressure in the line between the make-up pump (an on-line dilution pump which dilutes the flow which enters the MS instrument before the second flow splitter) and the probe must be less than the back pressure in the line between the post column input and the fraction collection. In order to achieve the desired pressure, one can change the tubing requirements from standard HPLC devices to provide wider diameters to handle the increased flow rates, and optionally use a UV/DAD (diode array detector) or other suitable detector to trigger fraction collection.

The following steps can optionally be performed. Information gathered on the compounds (i.e., the UV absorbance and MS information) can be stored in a relational database, preferably with other information about the compounds (i.e., synthesis conditions, bioassay information, yield, etc.). The compounds can be further characterized, for example, by $^1$H NMR. To more rapidly purify compounds, the HPLC can include two or more columns, one of which purifies compounds while the other(s) is/are being cleaned and regenerated. This step removes the chromatographic equilibration downtime.

Types of Compounds which can be Purified

Virtually any organic compound which is capable of being eluted on an HPLC column can be purified according to the methods described herein. Preferably, the compounds to be purified are part of a library of compounds, more preferably, a lead generation or combinatorial library of compounds. The purity capable of being obtained using the method is typically greater than 90%, and is preferably greater than 95%.

The term "library" refers to at least 3, preferably from $10^2$ to $10^9$ and more preferably from $10^2$ to $10^4$ compounds.

Preferably, these compounds are prepared as a multiplicity of compounds in a single solution or reaction mixture which permits facile synthesis thereof. Each member of the library of compounds can be isolated and, optionally, characterized.

Typically, the compounds have a core structure which can be modified at least one position, preferably two or more positions, with a variety of different functional groups, in order to generate a library, for example, a combinatorial or lead optimization library of compounds.

Typical core structures are linear, branched or cyclic organic compounds that include at least three carbon atoms and at least one, and preferably at least two sites capable of undergoing a reaction to change the structure, usually by the addition of other molecules to the reactive site.

Examples of families of insecticides include 1-aryl pyrazoles, pyrroles, pyrrolidones, and nicotinic acid derivatives. However, ligand compounds which may bind to the appropriate binding site may be, for example, steroids, hormones, peptides, proteins, oligonucleotides, oligoribonucleotides, enzymes, and the like.

Suitable core structures include, but are not limited to: peptides, proteins, oligonucleotides, oligoribonucleotides, oligosaccharides, alkaloids, quinolines, isoquinolines, benzimidazoles, benzothiazoles, purines, pyrimidines, thiazolidines, imidazopyrazinones, oxazolopyridines, pyrroles, pyrrolidines, imidazolidones, guinolones, amino acids, macrolides, penems, saccharides, xanthins, benzothiadiazine, anthracyclines, dibenzocycloheptadienes, inositols, porphyrins, corrins, and carboskeletons presenting geometric solids (e.g., dodecahedrane). The core structures can be derived from naturally occurring compounds, or can include non-natural modifications (i.e., non-naturally occurring amino acids and nucleotides).

Suitable modifications for the core structures include:

1) amino acid derivatives, which include, for example, natural and synthetic amino acid residues including all of the naturally occurring alpha amino acids, species having derivatives, variants or mimetics of the naturally occurring side chains; N-substituted glycine residues; natural and synthetic species known to functionally mimic amino acid residues, such as statin, bestatin, etc.

2) nucleotide derivatives, which includes natural and synthetic nucleotides, such as adenosine, thymine, guanidine, uridine, cytosine, derivatives of these and variants and mimetics of the purine ring, the sugar ring, the phosphate linkage and combinations of some or all of these. Nucleotide probes (between 2 and 25 nucleotides) and oligonucleotides (more than 25 nucleotides) including all of the various possible structural modifications; homo and hetero-synthetic combinations and permutations of the naturally occurring nucleotides; derivatives and variants containing synthetic purine or pyrimidine species, or mimics of these; various sugar ring mimetics; and a wide variety of alternate backbone analogs, including but not limited to phosphodiester, phosphorothionate, phosphorodithionate, phosphoramidate, alkyl phosphotriester, sulfamate, 3'-thioformacetal, methylene(methylimino), 3-N-carbamate, morpholino carbamate and peptide nucleic acid analogs.

3) a carbohydrate derivative, which would include natural physiologically active carbohydrates; related compounds, such as glucose, galactose, sialic acids, beta-D-glucosylamine and nojorimycin, which are both inhibitors of glucosidase; pseudo sugars, such as 5a-carba-2-D-galactopyranose, which is known to inhibit the growth of Klebsiella pneumonia (n=1); synthetic carbohydrate residues and derivatives of these (n=1) and all of the complex oligomeric permutations of these as found in nature, including high mannose oligosaccharides, the known antibiotic streptomycin (n>1).

4) a naturally occurring or synthetic organic structural motif. The term "motif" is defined as an organic molecule having or containing a specific structure that has biological activity, such as a molecule having a complementary structure to an enzyme active site, for example. This term includes any of the well known basic structures of pharmaceutical compounds including pharmacophores, or metabolites thereof. These basic structures include beta-lactams, such as penicillin, known to inhibit bacterial cell wall biosynthesis; dibenzazepines, known to bind to CNS receptors and used as antidepressants; polyketide macrolides, known to bind to bacterial ribosymes, etc. These structural motifs are generally known to have specific desirable binding properties to ligand acceptors.

5) a reporter element, such as a natural or synthetic dye or a residue capable of photographic amplification which possesses reactive groups that may be synthetically incorporated into the sulfaminimide structure or reaction scheme, and may be attached through the groups without adversely interfering or affecting with the reporting functionality of the group. Preferred reactive groups are amino, thio, hydroxy, carboxylic acid, carboxylic acid ester, particularly methyl ester, acid chloride, isocyanate alkyl halides, aryl halides and oxirane groups.

6) an organic moiety containing a polymerizable group such as a double bond, or other functionalities capable of undergoing condensation polymerization or copolymerization. Suitable groups include vinyl groups, oxirane groups, carboxylic acids, acid chlorides, esters, amides, azlactones, lactones and lactams. Other organic moiety such as those defined for R and R' may also be used.

7) a macromolecular component, such as a macromolecular surface or structures which may be attached to the sulfaminimide modules via the various reactive groups outlined above, in a manner where the binding of the attached species to a ligand-receptor molecule is not adversely affected and the interactive activity of the attached functionality is determined or limited by the macromolecule. Examples of macromolecular components include porous and non-porous inorganic components, such as, for example, silica, alumina, zirconia, titania and the like, as commonly used for various applications, such as normal and reverse phase chromatographic separations, water purification, pigments for paints, etc.; porous and non-porous organic macromolecular components, including synthetic components such as styrenedivinyl benzene beads, various methacrylate beads, PVA beads, and the like, commonly used for protein purification, water softening; and a variety of other applications, natural components such as native and functionalized celluloses, such as, for example, agarose and chitin, sheet and hollow fiber membranes made from nylon, polyether sulfone or any of the materials mentioned above. The molecular weight of these macromolecules may range up to about 2000 Daltons.

Suitable chemical modifications also include chemical bonds to a suitable organic moiety, a radioactive moiety, a hydrogen atom, an organic moiety which contains a suitable electrophilic group, such as an aldehyde, ester, alkyl halide, ketone, nitrile, epoxide or the like; a suitable nucleophilic group, such as a hydroxyl, amino, carboxylate, amide, carbanion, urea or the like; or one of the other structural diversity elements defined below. In addition, the chemical modifications can be in the form of a ring, bi-cyclic or tri-cyclic ring system; or structure which connects to the ends of the repeating unit of the compound defined by the preceding formula; or may be separately connected to other moieties.

The modifications can be the same or different and each may be one or more atoms of carbon, nitrogen, sulfur, oxygen, any other inorganic elements or combinations thereof. For example, the core structure can be modified with cyano, nitro, halogen, oxygen, hydroxy, alkoxy, thio, straight or branched chain alkyl, carbocyclic aryl and substituted or heterocyclic derivatives thereof. The modifications can be in different in adjacent molecular cores and have a selected stereochemical arrangement about the carbon atom to which they are attached.

The compounds can be laid out in a logical fashion in multi-tube arrays or multi-well plates, in the form of arrays of chemical compounds. Preferably, the compounds all have a central core structure, and have various modifications which permit the identification of structure-activity relationships with which to determine optimum compounds for a particular use.

The array can be ordered in such a fashion as to expedite synthesis, purification, and evaluation, to maximize the informational content obtained from the testing and to facilitate the rapid evaluation of that data.

The arrays can be constructed from logically ordered and arranged sub-arrays of compounds. Sub-arrays can be prepared which include spatially addressable sets of structurally related individual chemical compounds, with a common structure and a variable modification of the structure. Sub-arrays are particular useful when multiple positions on the structure are modified, and the variation between any two compounds within a given sub-array can include, for example, zero (0) or one (1) change in a structure.

These sub-arrays and arrays can be organized to form higher order arrays that include sets of arrays, and can be evaluated as a higher order array to provide information regarding the optimum structural features for the common core structure of interest.

The sub-arrays can be arranged in such a manner that the direct comparisons of compounds automatically yields information regarding the effect known fragments have on a desired application, as well as on the effect on changes in physical and reactive properties. As provided by simple set theory for any number of independently variable structural diversity elements n, there exists n logical higher order array arrangements, such that relational information on the effect of variation of each of the n structural diversity elements can be obtained in a similar manner by comparison of testing data from the relative addresses in appropriately arranged sub-arrays.

By screening all possible synthetic variations of a core molecule, the selection of the optimal candidate is more a function of the data collection method than the "rational" basis for selecting the compound. The desired physical and chemical properties, i.e., binding affinity and bioactivity, can be rapidly optimized, and directly correlated with the structural changes within a particular array or sub-array.

Because the spatial address of each compound within a multi-tube rack is known, the arrays can be tested to generate complete relational structural information such that a positive result provides: (1) information on a compound within any given spatial address; (2) simultaneous juxtaposition of this information upon a set of systematically structural congeners; (3) the ability to extract relational structural information from negative results in the presence of positive results.

Preferably, the purification is carried out via computer control, where the location of each tube in a multi-tube array or each well in a multi-well plate is stored in a computer, and the identity of the compound to be synthesized is stored in the computer in a "memory map" or other means for correlating the data for the compound to the position of the tube or well. Alternatively, the purification can be performed manually, preferably in multi-tube racks or multi-well plates, and the information stored on a computer. The compounds in the tubes can be purified and/or characterized.

The present invention will be further understood with reference to the following non-limiting examples:

EXAMPLE 1

Analytical Methods

A series of compounds were evaluated on a TLC plate with a C18 backing using an 80/20 v/v methanol/water solvent system. The compounds were found to have one of four ranges of retention factors (Rfs), Rf=0, 0.05<Rf<0.2, 0.2<Rf<0.8, or Rf>0.8.

Those compounds which did not have an Rf=0 were eluted off of a 5 micron, 50 mm C18 reverse phase HPLC column with an internal diameter of 4.6 mm. The compounds were eluted using various gradients of two solvent systems, solvent A (water/acetonitrile 98/1.5 (v/v)) and solvent B (100% methanol).

Those compounds with an Rf between 0.2 and 0.8 were eluted using protocol I or II as described below. Those compounds with an Rf between 0.05 and 0.2 were eluted using protocol II or III as described below. Those compounds with an Rf greater than 0.8 were eluted using protocol I or IV as described below. The protocols are presented below in tabular form.

TABLE 1

Protocol I (analytical)

| Time (min) | Flow rate (mL/min) | % A | % B |
| --- | --- | --- | --- |
| 0.0 | 1.5 | 75 | 25 |
| 5.0 | 1.5 | 5 | 95 |
| 6.0 | 1.5 | 0 | 100 |
| 8.0 | 1.8 | 75 | 25 |

TABLE 2

Protocol II (analytical)

| Time (min) | Flow rate (mL/min) | % A | % B |
| --- | --- | --- | --- |
| 0.0 | 1.5 | 45 | 55 |
| 5.0 | 1.5 | 0 | 100 |
| 6.0 | 1.5 | 0 | 100 |
| 8.0 | 1.8 | 45 | 55 |

TABLE 3

Protocol III (analytical)

| Time (min) | Flow rate (mL/min) | % A | % B |
| --- | --- | --- | --- |
| 0.0 | 1.5 | 30 | 70 |
| 5.0 | 1.5 | 0 | 100 |

TABLE 3-continued

Protocol III (analytical)

| Time (min) | Flow rate (mL/min) | % A | % B |
| --- | --- | --- | --- |
| 6.0 | 1.5 | 0 | 100 |
| 8.0 | 1.8 | 30 | 70 |

TABLE 4

Protocol IV (analytical)

| Time (min) | Flow rate (mL/min) | % A | % B |
| --- | --- | --- | --- |
| 0.0 | 1.5 | 95 | 5 |
| 5.0 | 1.5 | 5 | 95 |
| 6.0 | 1.5 | 0 | 100 |
| 8.0 | 1.8 | 95 | 5 |

These four protocols on an analytical column can be scaled up to the following four protocols (shown below in tables 5–8) on a preparative HPLC column (50×20 mm id with a C18 sorbent with a particle size of 5 microns or less).

TABLE 5

Protocol I (preparative)

| Time (min) | Flow rate (mL/min) | % A | % B |
| --- | --- | --- | --- |
| 0.0 | 28.0 | 90 | 10 |
| 5.0 | 28.0 | 75 | 25 |
| 6.0 | 30.0 | 5 | 95 |
| 7.0 | 25.0 | 0 | 100 |
| 9.0 | 25.0 | 90 | 10 |

TABLE 6

Protocol II (preparative)

| Time (min) | Flow rate (mL/min) | % A | % B |
| --- | --- | --- | --- |
| 0.0 | 15 | 70 | 30 |
| 1.0 | 28 | 45 | 55 |
| 6.0 | 28 | 0 | 100 |
| 7.0 | 28 | 0 | 100 |
| 9.0 | 30.0 | 70 | 30 |

TABLE 7

Protocol III (preparative)

| Time (min) | Flow rate (mL/min) | % A | % B |
| --- | --- | --- | --- |
| 0.0 | 15.0 | 45 | 55 |
| 1.0 | 28.0 | 30 | 70 |
| 6.0 | 28.0 | 0 | 100 |
| 7.0 | 28.0 | 0 | 100 |
| 9.0 | 30.0 | 45 | 55 |

TABLE 8

Protocol IV (preparative)

| Time (min) | Flow rate (mL/min) | % A | % B |
|---|---|---|---|
| 0.0 | 15.0 | 98 | 2 |
| 1.0 | 28.0 | 95 | 5 |
| 6.0 | 28.0 | 5 | 95 |
| 7.0 | 28.0 | 0 | 100 |
| 9.0 | 30.0 | 98 | 2 |

In this example, the auto-injector was a Gilson 215 liquid handler with an 819 injection valve actuator. The fraction collector was a Gilson 215 liquid handler. The gradient pumps were two Gilson pump 306 models with 50 SC pump heads. The dilution pumps were Gilson 307 pumps with 1.5 SC pump heads. The equilibration pump was a programmable HPLC Gilson pump 305 model with a 50 SC pump head. The mixer was a Gilson 811 C dynamic mixer with an 806 Monometric model. The pressure monitor was a Gilson 806 model pressure monitor. The HPLC detectors used were a Gilson 170 model diode array detector with a MS detector Platform LC model from micromass. The MS detector contains a quadruple mass analyzer with atmospheric pressure ionization (API) source capable of using both atmospheric chemical ionization (APCI) and Megaflow electrospray ionization probes. The mass spectrometer is equipped with a rotary pump and a transformer. The switching valves were two Gilson valve mates and a 10 port Rheodyne switching valve. The splitter was one 1/1000 ACURATE by LC packing and an Upchurch splitter. The data collection system was a Digital CELEB GL-2 computer, monitor and Hewlett Packard Laser Jet 6P printer that included micromass Masslynx NT 3.1B6 work under Windows NT V. 4.0, OpenLynx Version™, FractionLynx™ and Gilson's Unipoint v. 1.64 software.

Figure 1:
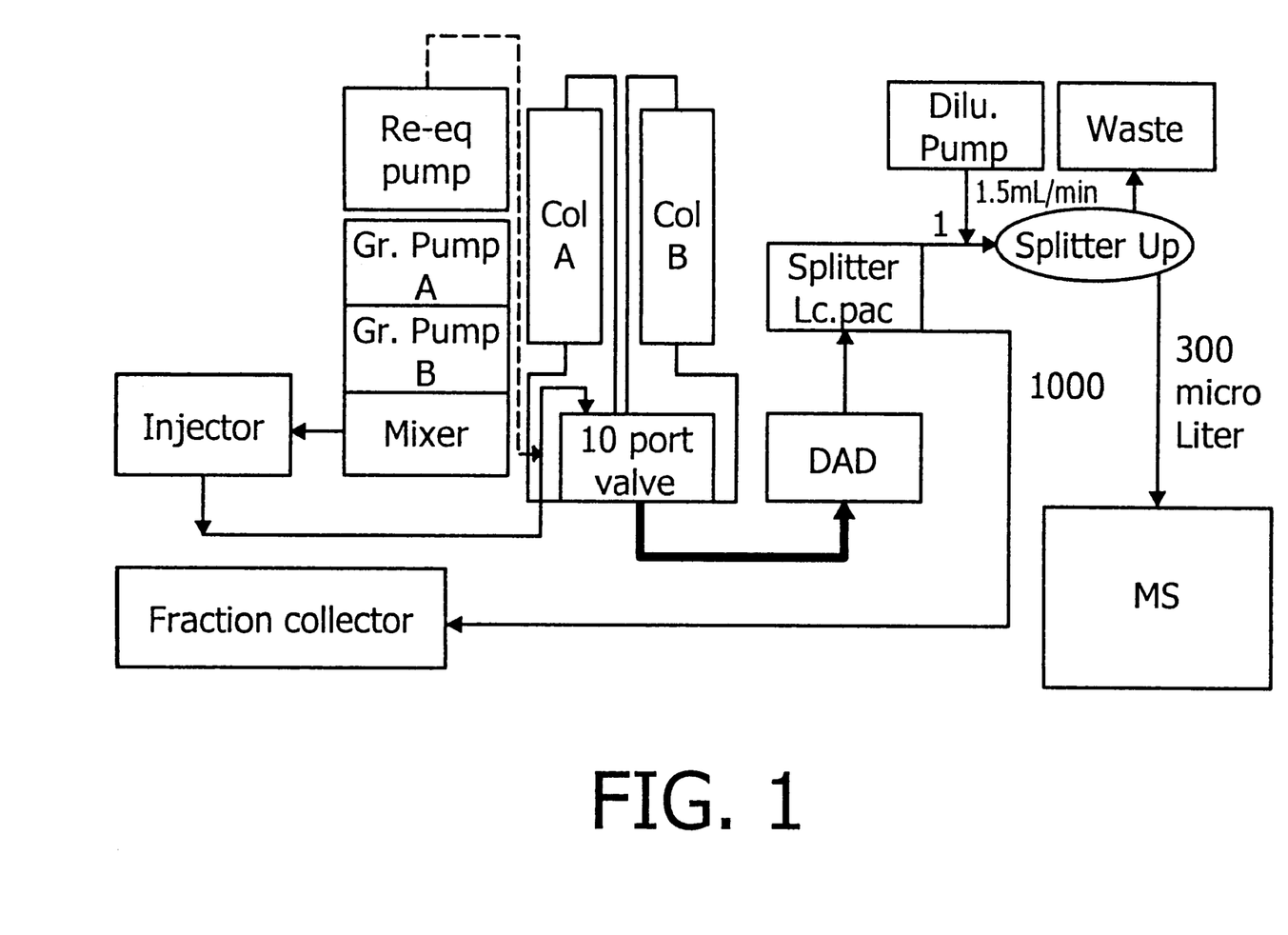
FIG. 1 is a diagram of the automated prep-HPLC/UV/MS system used in Example 1 (discussed below) illustrating the path of sample isolation.

The automated prep-HPLC/UV/MS was assembled as shown in FIG. 1.

The tubing sizes for the system are as follows:

From the mixer to the injector, the injector to the column, the column to the UV diode array detector and from the UV to the splitter box was Green Peek, Upchurch Scientific, INC 0.03" ID. From the make-up pump to the splitter box was Green Peek, Upchurch Scientific, INC 0.01" ID. From the splitter box to the upchurch splitter was Green Peek, Upchurch Scientific, INC 0.007" ID. From the Upchurch splitter to the waste reservoir was Green Peek, Upchurch Scientific, INC 0.01" ID. From the splitter to the fraction collector was 0.04" ID (Tubing Accurate/FC cat. No. PE-1000 FC).

The tubing sizes permitted the use of a 30 mL/min flow rate and a relatively small sorbent particle size (5 microns or less) with the purification method described below. With the smaller tubing sizes typically found in conventional HPLCs, it would be extremely difficult to achieve this high of a flow rate, and, accordingly, it would be extremely difficult to perform the purification method.

FIG. 1 illustrates the path of sample isolation during an HPLC run. After injection, the solvents from the gradient pump separate the components in column A while column B is being re-equilibrated by the re-equilibration pump. A ten port Rheodyne switching valve controls this action. The separated components enter into the UV diode array detector and then go to the splitter box. At the splitter box, the flow splits in a 1/1000 ratio. Only one part goes to the MS and the remainder goes to the waste reservoir after the compound of interest is detected by UV or MS, and the fraction collection is triggered and the sample collected. The flow that goes to the MS is diluted by a dilution pump with a flow of 1.5 mL/min for the electrospray (ESP) probe. Then, the diluted flow is split again by a second splitter (an Upchurch splitter) and only approximately 300 μL enters the ESP probe and the remainder is sent to waste. A second splitter is not required for the atmospheric pressure chemical ionization (APCI) probe. The gradient pumps were controlled using Unipoint software.

The delay time when the MS is seeing a peak and when the peak reaches the fraction collector, as well as the delay time between the UV detector and the MS were measured using coumarin as a standard, using a methanol/water (50/50) mobile phase, and are shown below in Table 9.

TABLE 9

| Probe | Gradient flow rate (mL/min) | Make-up flow rate (mL/min) | Time delay (second) MS-FC | Time delay (second) UV-MS |
|---|---|---|---|---|
| ESP | 22 | 1.5 | 20 | 3.5 |
|  | 28 | 1.5 | 15 | 9 |
|  | 30 | 1.5 | 15 | 9 |
| APCI | 22 | 0.5 | 12 | 23 |
|  | 28 | 0.5 | 15 | 12 |
|  | 30 | 0.5 | 15 | 12 |

The mass spectrometer was calibrated with PEG 200 to PEG 1000 for mass calibration prior to delay time measurement. The mass spectrometer was tuned with two probes at different flow rates.

A variety of compounds were passed through the HPLC column using the methods described herein. The compounds had molecular weights ranging from 100–650 g/mol, with sample sizes ranging from 0.1 to 200 mg, and injection volumes ranging from 50 to 2000 microliters.

The following example illustrates the use of the high throughput method for purification.

EXAMPLE 2
Purification of a Small Library of Compounds

Figure 2:
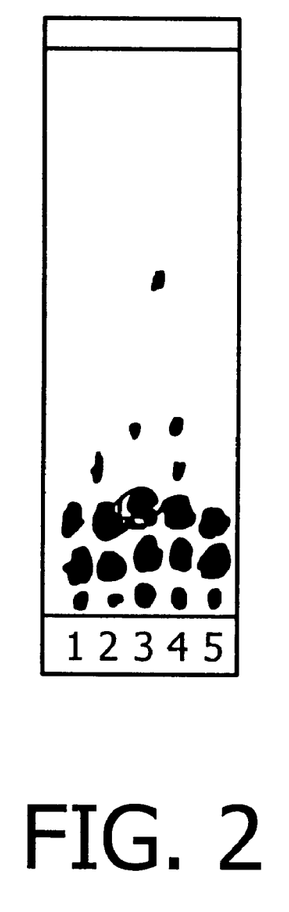
FIG. 2 is a TLC of the proprietary compounds used in Example 2 (discussed below).

A proprietary library of compounds was selected, and a TLC of 5 of the compounds was obtained, using 80/20 methanol/water as eluent. The TLC is shown in FIG. 2.

The TLC Rfs were calculated as being approximately 0.11 and correlated to pre-defined analytical HPLC methods (methods II or III in Example 1). Methods II and III were separately evaluated to determine which provided the best separations. The chromatograms showed that method II was better at purifying the compound from the impurities.

The compounds of interest were purified on a preparative HPLC column, with an injection volume of 2 mL, and a concentration of 150 mg compound/2 mL DMF. The compounds had retention times of between three and three and a half minutes on the preparative HPLC column.

Following the purification of the representative sample of compounds, a TLC was done on the entire library. The TLC showed that all of the compounds of interest elute with approximately the same Rf (about 0.1).

The preparative HPLC method was applied to all 450 compounds in the library, and an average purity of 91% was obtained, with an average yield of 28 mg. More than 85% of the compounds had a purity greater than 95%.

Those skilled in the art will recognize, or be able to ascertain using no more than routine experimentation, many equivalents to the specific embodiments of the invention described herein. Such equivalents are intended to be encompassed by the following claims.

What is claimed is:

1. A method for purifying and/or characterizing one or more organic compounds, comprising the steps of:

a) selecting a library of compounds to be purified b) performing a TLC and/or an analytical HPLC on a representative sample of the library, which sample comprises less than ten percent of the library, c) determining a correlated preparative HPLC method depending on how the representative sample elutes off the analytical HPLC column and/or the sample moves on a TLC plate, and d) purifying all or substantially all of the library, wherein the correlated preparative HPLC method is determined based on a correlation between three or more zones of retention times if analytical HPLC is performed and/or three or more zones of retention factors if TLC is performed, such that if substantially all of the compounds in the representative sample fall within a particular zone, a correlated preparative HPLC protocol can be used to purify compounds that fall within the zone.

2. The method according to claim 1, wherein both analytical HPLC and TLC are performed in step a.

3. The method according to claim 1, wherein the representative sample is purified via preparative HPLC before all or substantially all of the library is purified.

4. The method according to claim 3, wherein after the representative sample is purified, the purity of the compounds in the sample is determined.

5. The method according to claim 4, wherein after the purity is determined, a TLC is performed on between 10 and 100 percent of the library under the same or substantially the same conditions as the TLC performed in step a.

6. The method according to claim 5, wherein the TLC of the representative sample and the 10 to 100 percent of the library are compared.

7. The method according to claim 6, wherein if the TLC of the representative sample and the 10 to 100 percent of the library show that the compounds move into the same zone, then the entire library is purified via preparative HPLC.

8. The method according to claim 6, wherein if the TLC of the representative sample and the 10 to 100 percent of the library show that the compounds do not move into the same zone, then the entire library is purified via preparative HPLC using an alternative method.

9. The method according to claim 5, wherein between 50 and 100 percent of the library is analyzed via TLC.

10. The method according to claim 1, wherein the representative sample is between 2 and 5 percent of the entire library.

11. The method of claim 1, wherein during the preparative HPLC of all or substantially all of the library, fraction collection is triggered by determining the presence of the compound of interest in a sample which is eluting off of the preparative HPLC column using UV and/or MS detection.

12. The method of claim 1, wherein the purity of all or substantially all of the compounds purified via preparative HPLC is greater than 90 percent.

13. The method of claim 12, wherein analytical HPLC is performed, if at all, only on a representative sample prior to performing preparative HPLC.

* * * * *